United States Patent
Kobayashi et al.

(10) Patent No.: US 11,186,831 B2
(45) Date of Patent: Nov. 30, 2021

(54) MUTANT POLYHYDROXYALKANOATE SYNTHASE, GENE THEREOF AND TRANSFORMANT, AND METHOD FOR PRODUCING POLYHYDROXYALKANOATE

(71) Applicant: KANEKA CORPORATION, Osaka (JP)

(72) Inventors: Shingo Kobayashi, Takasago (JP); Shinichi Yoshida, Takasago (JP); Shunsuke Sato, Takasago (JP); Naoaki Taoka, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/962,282

(22) PCT Filed: Jan. 10, 2019

(86) PCT No.: PCT/JP2019/000453
§ 371 (c)(1),
(2) Date: Jul. 15, 2020

(87) PCT Pub. No.: WO2019/142717
PCT Pub. Date: Jul. 25, 2019

(65) Prior Publication Data
US 2020/0354696 A1    Nov. 12, 2020

(30) Foreign Application Priority Data

Jan. 16, 2018 (JP) .............................. JP2018-004678

(51) Int. Cl.
| | |
|---|---|
| *C12N 9/10* | (2006.01) |
| *C12P 7/10* | (2006.01) |
| *C12N 1/20* | (2006.01) |
| *C12N 15/00* | (2006.01) |
| *C12P 7/62* | (2006.01) |
| *C12N 15/74* | (2006.01) |
| *C12N 15/09* | (2006.01) |

(52) U.S. Cl.
CPC ............ *C12N 9/1029* (2013.01); *C12N 15/09* (2013.01); *C12N 15/74* (2013.01); *C12P 7/625* (2013.01)

(58) Field of Classification Search
CPC ................. C12N 9/1029; C12P 7/625
See application file for complete search history.

(56) References Cited

U.S. PATENT DOCUMENTS

| | | | | |
|---|---|---|---|---|
| 5,849,894 A | * | 12/1998 | Clemente ........... | C12N 15/8243 536/23.2 |
| 2005/0009949 A1 | | 1/2005 | Doi et al. | |
| 2018/0305722 A1 | | 10/2018 | Kobayashi et al. | |
| 2018/0371509 A1 | | 12/2018 | Arikawa et al. | |

FOREIGN PATENT DOCUMENTS

| | | |
|---|---|---|
| JP | 2015-77103 A | 4/2015 |
| WO | WO 03/050277 A1 | 6/2003 |
| WO | WO 2017/056442 A1 | 4/2017 |
| WO | WO 2017/104722 A1 | 6/2017 |

OTHER PUBLICATIONS

E1SNA2_FERBD. UniProtKB Database. 2016.*
Studer. Residue mutations and their impact on protein structure and function: detecting beneficial and pathogenic changes. Biochem. J. (2013) 449, 581-594.*
Fukui. Cloning and analysis of the poly(3-hydroxybutyrate-co-3-hydroxyhexanoate) biosynthesis genes of Aeromonas caviae. J. Bacteriol. 179:4821-4830(1997).*
International Search Report dated Mar. 26, 2019 in PCT/JP2019/000453 filed on Jan. 10, 2019, citing documents AA-AC, AO-AR, and AX-AY therein, 2 pages.
Kichise et al., "Enhanced Accumulation and Changed Monomer Composition in Polyhydroxyalkanoate (PHA) Copolyester by In Vitro Evolution of *Aeromonas caviae* PHA Synthase", Applied and Environmental Microbiology, 2002, vol. 68, No. 5, pp. 2411-2419.
Tsuge et al., "Combination of N149S and D171G mutations in *Aeromonas caviae* polyhydroxyalkanoate synthase and impact on polyhydroxyalkanoate biosynthesis", FEMS Microbiol. Lett., 2007, vol. 277, pp. 217-222.

* cited by examiner

*Primary Examiner* — Yong D Pak
(74) *Attorney, Agent, or Firm* — Oblon, McClelland, Maier & Neustadt, L.L.P.

(57) ABSTRACT

Provided is a mutant PHA synthase which produces of a PHA copolymer with a high or low 3HH ratio while maintaining PHA productivity. The mutant PHA synthase is a mutant polyhydroxyalkanoate synthase having an amino acid sequence having 85% or more sequence identity with the amino acid sequence of SEQ ID NO: 1 and having at least one of the following mutations (a) to (c): (a) a substitution of serine at 389th position from N-terminus of the amino acid sequence of SEQ ID NO: 1 with an amino acid other than serine; (b) a substitution of leucine at 436th position from the N-terminus of the amino acid sequence of SEQ ID NO: 1 with an amino acid other than leucine; and (c) a deletion of 11 to 19 amino acid residues from the C-terminus of the amino acid sequence of SEQ ID NO: 1.

16 Claims, No Drawings

Specification includes a Sequence Listing.

MUTANT POLYHYDROXYALKANOATE SYNTHASE, GENE THEREOF AND TRANSFORMANT, AND METHOD FOR PRODUCING POLYHYDROXYALKANOATE

TECHNICAL FIELD

The present invention relates to a mutant polyhydroxyalkanoate synthase, a gene encoding the enzyme, a transformant having the gene, and a method for producing polyhydroxyalkanoate using the transformant.

BACKGROUND ART

Polyhydroxyalkanoate (hereinafter, abbreviated as "PHA") is thermoplastic polyester produced and accumulated as an energy storage substance in cells of many microbial species. PHA, which is produced from various natural carbon sources by microorganisms, is an environmentally friendly plastic that is completely biodegraded by microorganisms in soil and water.

As PHA, poly-3-hydroxybutyrate (hereinafter, abbreviated as "PHB"), which is a homopolymer of 3-hydroxybutyrate (hereinafter, abbreviated as "13HB"), is known, and PHB has high crystallinity and a high crystallinity degree, and is therefore hard and brittle. In addition, PHB has a problem of low melt processability.

As PHA in which the brittleness and the melt processability of PHB are improved, poly(3HB-co-3HH) (hereinafter, abbreviated as "PHBH"), which is copolymer polyester of 3HB and 3-hydroxyhexanoate (hereinafter, abbreviated as "3HB") has been reported. PHBH is a copolymer which has 3HH as a monomer unit, and thus has a lower crystallinity degree as compared to PHB, and a physical property of being flexible and soft.

As a method for producing PHBH, it has been reported that PHBH is produced by fermentation using a transformant obtained by introducing a PHA synthase derived from *Aeromonas caviae* into *Cupriavidus necator*, which is a soil bacterium, as a host. In order to enhance the flexibility of PHBH, studies are being conducted for increasing the 3HH ratio in PHBH.

NPTLs 1 and 2 describe methods for introducing a mutation into a PHA synthase in order to increase the 3HH ratio in PHBH. Specifically, NPTL 1 reports that a mutation of substitution of asparagine at the 149th position with serine or substitution of aspartic acid at the 171st position with glycine is introduced into an *A. caviae*-derived PHA synthase to improve the activity of PHA synthase and the substrate specificity to 3HH-CoA, so that PHBH having a 3HH ratio of maximum 18 mol % can be produced.

Further, in NPTL 2 reports that PHBH with a higher 3HH ratio can be produced with the aid of a PHA synthase in which these two mutations are overlapped (hereinafter, abbreviated as "NSDG").

CITATION LIST

Non Patent Literature

NPTL 1: T. Kichise, S. Taguchi, Y Doi, App. Environ. Microbiol., 68, pp. 2411-2419 (2002).
NPTL 2: T. Tsuge, S. Watanabe, D. Shimada, H. Abe, Y Doi, S. Taguchi, FEMS Microbiol. Lett., 277, pp. 217-222 (2007).

SUMMARY OF INVENTION

Technical Problem

Currently, the 3HH ratio of a PHA copolymer that can be produced by culturing a transformant is limited. Further, in production of PHA having preferred physical properties, the 3HH ratio is not necessarily preferably as high as possible the better, and therefore a technique for freely adjusting the 3HH ratio to a higher or lower level is required. Thus, it is desired to construct a PHA synthase library which enables production of a PHA copolymer with a higher or lower 3HH ratio.

Accordingly, an object of the present invention is to provide a mutant PHA synthase which enables production of a PHA copolymer with a high or low 3HH ratio while maintaining PHA productivity; a gene encoding the enzyme; a transformant having the gene; and a method for producing PHA using the transformant.

Solution to Problem

The present inventors have extensively conducted studies for solving the above-described problems, and resultantly found that introduction of a mutation to serine at the 389th position, introduction of a mutation to leucine at the 436th position or deletion of the C-terminus region in a PHA synthase enables production of PHA copolymers having different 3HH ratios while maintaining PHA productivity, leading to completion of the present invention.

That is, the present invention provides a mutant polyhydroxyalkanoate synthase having an amino acid sequence having 85% or more sequence identity with an amino acid sequence of SEQ ID NO: 1 and comprising any one or more of mutations (a) to (c) below.

Mutation (a): mutation of substitution of serine at 389th position from N-terminus of the amino acid sequence of SEQ ID NO: 1 with an amino acid other than serine Mutation (b): mutation of substitution of leucine at 436th position from the N-terminus of the amino acid sequence of SEQ ID NO: 1 with an amino acid other than leucine Mutation (c): mutation of deletion of 11 or more and 19 or less amino acid residues from C-terminus of the amino acid sequence of SEQ ID NO: 1

Preferably, the mutation (a) is a mutation of substitution of serine at the 389th position from the N-terminus of the amino acid sequence of SEQ ID NO: 1 with cysteine, isoleucine, threonine or valine.

Preferably, the mutation (a) is a mutation of substitution of serine at the 389th position from the N-terminus of the amino acid sequence of SEQ ID NO: 1 with aspartic acid, glutamic acid, glycine, histidine, lysine, asparagine, proline, arginine or tryptophan.

Preferably, the mutation (b) is a mutation of substitution of leucine at the 436th position from the N-terminus of the amino acid sequence of SEQ ID NO: 1 with valine. Preferably, the mutation (b) is a mutation of substitution of leucine at the 436th position from the N-terminus of the amino acid sequence of SEQ ID NO: 1 with alanine, cysteine, phenylalanine, asparagine, threonine, tryptophan or tyrosine.

Preferably, the mutation (c) is a mutation of deletion of 12 to 19 amino acid residues from the C-terminus of the amino acid sequence of SEQ ID NO: 1.

Preferably, the mutant polyhydroxyalkanoate synthase of the present invention has an amino acid sequence further including a mutation of substitution of asparagine at 149th position from the N-terminus of the amino acid sequence of SEQ ID NO: 1 with serine, and an amino acid sequence further including a mutation of substitution of aspartic acid at 171st position from the N terminus of the amino acid sequence of SEQ ID NO: 1 with glycine.

The present invention also relates to a gene encoding the mutant polyhydroxyalkanoate synthase.

Further, the present invention also relates to a transformant having the gene. The host is preferably the host is a bacterium, with the bacterium being more preferably a bacterium belonging to *Cupriavidus*, still more preferably *Cupriavidus necator*, even more preferably *Cupriavidus necator* H16.

The present invention also relates to a method for producing polyhydroxyalkanoate, including the step of culturing the transformant. Preferably, the polyhydroxyalkanoate contains 3-hydroxyhexanoate as a monomer unit. More preferably, the polyhydroxyalkanoate is a copolymer of 3-hydroxybutyrate and 3-hydroxyhexanoate.

Advantageous Effects of Invention

According to the present invention, it is possible to provide a mutant PHA synthase which enables production of a PHA copolymer with a high or low 3HH ratio while maintaining PHA productivity; a gene encoding the enzyme; and a transformant having the gene. In addition, by culturing the transformant, a PHA copolymer with a high or low 3HH ratio can be produced by fermentation without lowering the productivity of PHA.

DESCRIPTION OF EMBODIMENTS

Hereinafter, the present invention will be described in detail.

(Mutant PHA Synthase)

The mutant PHA synthase according to the present invention has an amino acid sequence having 85% or more sequence identity with the amino acid sequence of SEQ ID NO: 1, and includes any one or more of the following mutations (a) to (c). The present invention also provides a gene encoding the mutant PHA synthase (hereinafter, abbreviated as a "mutant PHA synthase gene").

The mutant PHA synthase of the present invention enables production of a PHA copolymer with a high or low 3HH ratio while maintaining PHA productivity. The high or low 3HH ratio of a PHA copolymer produced by the mutant PHA synthase of the present invention means being relatively high or low as compared to the 3HH ratio of a PHA copolymer which can be produced under the same conditions by a PHA synthase having an amino acid sequence identical to that of the mutant PHA synthase of the present invention except that a mutation as a characteristic of the present invention is not introduced.

The mutant PHA synthase of the present invention is an enzyme having PHA synthetizing activity, and has an amino acid sequence having 85% or more sequence identity with the amino acid sequence of SEQ ID NO: 1. The amino acid sequence of SEQ ID NO: 1 is an amino acid sequence of a PHA synthase PhaC$_{Ac}$ derived from *Aeromonas caviae*. The mutant PHA synthase of the present invention may have a mutation other than the following mutations (a) to (c) as long as the sequence identity is satisfied.

The mutant PHA synthase of the present invention may be one that forms a fusion protein by binding to a heterologous protein having a different function. In this case, the amino acid sequence of the heterologous protein is not considered in calculation of the sequence identity.

In the mutant PHA synthase of the present invention, the sequence identity with the amino acid sequence of SEQ ID NO: 1 may be 85% or more, and is preferably 90% or more, more preferably 95% or more, still more preferably 97% or more, even more preferably 98% or more, especially preferably 99% or more.

Regarding the nucleotide sequence of the mutant PHA synthase gene of the present invention, the sequence identity of the nucleotide sequence is not limited as long as the nucleotide sequence is a nucleotide sequence encoding an amino acid sequence which forms the mutant PHA synthase of the present invention.

The origin of the mutant PHA synthase and the mutant PHA synthase gene of the present invention is not particularly limited, and is preferably *Aeromonas*, more preferably *Aeromonas caviae*.

The mutations (a) to (c) contained in the mutant PAH synthase of the present invention will now be described. The mutant PAH synthase of the present invention may contain any one of the mutations (a) to (c), or two or more of these mutations.

Mutation (a): serine at the 389th position from the N-terminus is substituted with an amino acid other than serine in the amino acid sequence of SEQ ID NO: 1. The amino acid after the substitution can be selected with consideration given to PHA productivity and the 3HH ratio in PHA produced. For producing PHA with a low 3HH ratio by reducing 3HH-CoA specificity while maintaining PHA productivity, a mutation of substitution of serine at the 389th position with aspartic acid, glutamic acid, glycine, histidine, lysine, asparagine, proline, arginine or tryptophan is preferable, a mutation of substitution of serine at the 389th position with aspartic acid, glutamic acid, glycine, histidine, lysine, proline, arginine or tryptophan is more preferable, and a mutation of substitution of serine at the 389th position with aspartic acid, glutamic acid, lysine, proline or arginine is still more preferable. On the other hand, for producing PHA with a high 3HH ratio by increasing 3HH-CoA specificity while maintaining PHA productivity, a mutation of substitution of serine at the 389th position with cysteine, isoleucine, threonine or valine is preferable, and a mutation of substitution of serine at the 389th position with cysteine, threonine or valine is more preferable.

Mutation (b): leucine at the 436th position from the N-terminus in the amino acid sequence of SEQ ID NO: 1 is substituted with an amino acid other than leucine. The amino acid after the substitution can be selected with consideration given to PHA productivity and the 3HH ratio in PHA produced. For producing PHA with a low 3HH ratio by reducing 3HH-CoA specificity while maintaining PHA productivity, a mutation of substitution of leucine at the 436th position with alanine, cysteine, phenylalanine, asparagine, threonine, tryptophan or tyrosine is preferable, a mutation of substitution of leucine at the 436th position with alanine, cysteine, phenylalanine or threonine is more preferable, and a mutation of substitution of leucine at the 436th position with alanine or threonine is still more preferable. On the other hand, for producing PHA with a high 3HH ratio by increasing 3HH-CoA specificity while maintaining PHA productivity, a mutation of substitution of leucine at the 436th position with valine is preferable.

Mutation (c): the amino acid sequence in the C-terminus region is deleted in the amino acid sequence of SEQ ID NO: 1. This enables production of PHA with a low 3HH ratio by reducing 3HH-CoA specificity while maintaining PHA productivity. The upper limit of the number of amino acid residues to be deleted is preferably 19, more preferably 18, still more preferably 17, especially preferably 16, most preferably 15, in terms of the number of amino acid residues from the C-terminus. The lower limit of the number of amino acid residues to be deleted is preferably 11, more preferably 12, still more preferably 13, in terms of the number of amino acid residues from the C-terminus.

For enhancing PHA productivity, it is preferable that the amino acid sequence of the mutant PHA synthase of the present invention further includes a mutation of substitution of asparagine at the 149th position from the N-terminus with serine, and/or a mutation of substitution of aspartic acid at the 171st position from the N-terminus with glycine, in the amino acid sequence of SEQ ID NO: 1.

(Transformant Producing 3HH Unit-Containing Copolymer PHA)

The transformant of the present invention is a transformant having a gene encoding the mutant PHA synthase of the present invention, and is produced by introducing the gene into a host microorganism.

The host of the transformant of the present invention is not particularly limited, and any microorganisms such as funguses (molds, mushrooms, yeasts or the like), bacteria or archaea can be used, with bacteria being preferable. Preferred examples of the bacteria include bacteria belonging to *Ralstonia, Cupriavidus, Wautersia, Aeromonas, Escherichia, Alcaligenes* and *Pseudomonas*. From the viewpoint of safety and productivity, the bacteria are more preferably bacteria belonging to *Ralstonia, Cupriavidus, Aeromonas* or *Wautersia*, still more preferably bacteria belonging to the *Capriavidus* or *Aeromonas*, even more preferably bacterial belonging to *Cupriavidus*, especially preferably *Cupriavidus necator*, most preferably *Cupriavidus necator* H16 strain.

As a method for introducing the mutant PHA synthase gene of the present invention into a host microorganism in production of the transformant of the present invention, any method can be used. As an example, a known gene recombination technique may be used to introduce the mutant PHA synthase gene of the present invention onto a DNA such as a chromosome, a plasmid or a megaplasmid of a host microorganism, or a plasmid vector or artificial chromosome having the gene may be introduced into the host microorganism. However, from the viewpoint of retaining the introduced gene, a method in which the gene is introduced onto a chromosome or megaplasmid of a microorganism is preferable, and a method in which the gene is introduced onto a chromosome of a microorganism is more preferable.

Methods for site-specifically substituting or inserting any nucleotide sequence on a DNA of a microorganism, or methods for deleting any nucleotide sequence in a DNA of a microorganism are widely known to those skilled in the art, and can be used in production of the transformant of the present invention. Typical methods include, but are not particularly limited to, a method using a transposon and a homologous recombination mechanism (Ohman et al., J. Bacteriol., Vol. 162: p. 1068 (1985)); a method based on site-specific integration caused by a homologous recombination mechanism and loss caused by second-stage homologous recombination (Noti et al., Methods Enzymol., Vol. 154, p. 197 (1987)); and a method in which a sacB gene derived from *Bacillus subtilis* is made to coexist, and a microorganism strain with a gene lost by second-stage homologous recombination is easily isolated as a sucrose-containing medium resistant strain (Schweizer, Mol. Microbiol., Vol. 6, p. 1195 (1992); Lenz et al., J. Bacteriol., Vol. 176, p. 4385 (1994)). Examples of methods for introducing a vector into a microorganism include, but are not particularly limited, to calcium chloride methods, electroporation methods, polyethylene glycol methods and spheroplast methods.

As gene cloning and gene recombination techniques, techniques described in Sambrook, J. et al., Molecular Cloning, A Laboratory Manual, Cold Spring Harbor Laboratory Press (1989 or 2001) can be used.

In introduction of the mutant PHA synthase gene of the present invention, the gene can be linked to an arbitrary expression control sequence. In the present specification, the expression control sequence is described as a sequence consisting of a promoter and a Shine-Dalgarno sequence. As such an expression control sequence, for example, the expression control sequence of the phaC1 gene (SEQ ID NO: 2) or the expression control sequence of the phaP1 gene (SEQ ID NO: 3) of *Cupriavidus necator* can be used. Alternatively, an *Escherichia coli*-derived lac promoter (SEQ ID NO: 4) or trp promoter (SEQ ID NO: 5), or an artificially prepared lacUV5 promoter (SEQ ID NO: 6), trc promoter (SEQ ID NO: 7), tic promoter (SEQ ID NO: 8), tac promoter (SEQ ID NO: 9), lacN17 promoter (SEQ ID NO: 10) and the like can be linked to the SD sequence (SEQ ID NO: 11) derived from the *Cupriavidus necator* H16 strain, and used as the expression control sequence.

(Method for Producing PHA)

By culturing the transformant of the present invention, the transformant can be caused to produce PHA, followed by collecting the obtained PHA to produce PHA.

In production of PHA according to the present invention, it is preferable to culture the transformant in a medium containing a carbon source, and a nitrogen source, an inorganic salts and other organic nutrient sources which are nutrient sources other than the carbon source.

The carbon source is not particularly limited as long as it is a carbon source which can be consumed by the transformant of the present invention and which contains oil and/or fatty acids, and any carbon source can be used. Specific examples include oils such as palm oil, palm kernel oil, corn oil, coconut oil, olive oil, soybean oil, rapeseed oil and jatropha oil, and fractionated oils thereof, fatty acids such as lauric acid, oleic acid, stearic acid, palmitic acid and myristic acid, and derivatives thereof.

Examples of the nitrogen source include ammonia; ammonium salts such as ammonium chloride, ammonium sulfate and ammonium phosphate; peptone, meat extracts, and yeast extracts.

Examples of the inorganic salts include potassium dihydrogen phosphate, disodium hydrogen phosphate, magnesium phosphate, magnesium sulfate and sodium chloride.

Examples of other organic nutrient sources include amino acids such as glycine, alanine, serine, threonine and proline; and vitamins such as vitamin B1, vitamin B12 and vitamin C.

The conditions for culturing the transformant of the present invention, such as a culture temperature, a culture time, pH in culture and a medium, are not particularly limited, and may be conditions which are commonly used for culture of host microorganisms, e.g. microorganisms such as *Ralstonia, Cupriavidus, Wautersia, Aeromonas, Escherichia, Alcaligenes* and *Pseudomonas*.

The type of PHA produced in the present invention is not particularly limited as long as it is a PHA copolymer containing 3HH as a monomer unit. In particular, PHA copolymers obtained by polymerizing 3HH with one or more monomers selected from 2-hydroxyalkanoate, 3-hydroxyalkanoate (except for 3HH) and 4-hydroxyalkanoate having 4 to 16 carbon atoms are preferable, and P(3HB-co-3HH) which is a copolymer of 3-hydroxybutyrate and 3-hydroxyhexanoate is most preferable. The type of PHA produced can be appropriately selected according to the type of a PHA synthase gene of a microorganism used or a PHA synthase gene introduced separately, the type of a metabolic gene involved in PHA synthesis, the carbon source used for culture, and other culture conditions.

In the present invention, the method for recovery of PHA from bacterial cells after culturing the transformant is not particularly limited, and a known method can be used. As an example, PHA can be recovered by the following method. After completion of culture, bacterial cells are separated from a culture solution by a centrifuge or the like, and the bacterial cells are washed with distilled water, methanol or the like, and dried. PHA is extracted from the dried bacterial cells using an organic solvent such as chloroform. From the organic solvent solution containing PHA, bacterial cell components are removed by filtration or the like, and a poor solvent such as methanol or hexane is added to the filtrate to precipitate PHA. Further, the supernatant is removed by filtration or centrifugation, and dried to recover PHA.

The composition (mol %) of monomer units contained in the obtained PHA, such as 3HH units, can be analyzed by a gas chromatography method, a nuclear magnetic resonance method, or the like.

EXAMPLES

Hereinafter, the present invention will be described in further detail byway of examples, but the present invention is not limited to these examples.

The genetic manipulation described below can be performed with reference to Molecular Cloning (Cold Spring Harbor Laboratory Press (1989)). In addition, enzymes, cloning hosts and the like which are used for gene manipulation can be purchased from suppliers on the market, and used according to the instructions. The enzymes are not particularly limited as long as they can be used for gene manipulation.

(Production Example 1) Preparation of H16 ΔphaC1 Ptrc-phaJ4b dZ1,2,6 Strain

First, a plasmid for disrupting the phaC1 gene was prepared. A DNA fragment (SEQ ID NO: 12) having a nucleotide sequence upstream and downstream of the phaC1 gene was obtained by PCR using a synthetic oligo DNA. The obtained DNA fragment was digested with a restriction enzyme SwaI. This DNA fragment was linked to a vector pNS2X-sacB also digested with the SwaI and described in Japanese Patent Laid-Open No. 2007-259708. In this way, a gene disrupting plasmid vector pNS2X-sacB-phaC1UL having nucleotide sequences upstream and downstream of phaC1 was prepared.

Next, a ΔphaC1 Ptrc-phaJ4b dZ1,2,6 strain was prepared using pNS2X-sacB-phaC1UL. The pNS2X-sacB-phaC1UL was introduced into an *Escherichia coli* S17-1 strain (ATCC47055). The obtained transformant was mixed with a KNK005 trc-phaJ4b ΔphaZ1,2,6 strain (see International Publication No. 2015/115619) and cultured on Nutrient Agar medium (manufactured by Difco Company) to perform conjugation transfer.

The obtained culture solution was inoculated in a Simmons agar medium containing 250 mg/L kanamycin (sodium citrate: 2 g/L, sodium chloride: 5 g/L, magnesium sulfate heptahydrate: 0.2 g/L, ammonium dihydrogen phosphate: 1 g/L, dipotassium hydrogen phosphate: 1 g/L, agar: 15 g/L, pH: 6.8) to obtain a strain with pNS2X-sacB-phaC1UL integrated on the chromosome of a KNK005 trc-phaJ4b ΔphaZ1,2,6 strain. This strain was subjected to two-generation culture in Nutrient Broth medium (manufactured by Difco Company), and then diluted and applied onto Nutrient Agar medium containing 15% of sucrose to obtain a strain in which a plasmid had been lost. From the obtained transformants, one strain deleting a region from the start codon to the stop codon of the phaC1 gene on a chromosome was isolated by PCR and analysis with a DNA sequencer. This gene-disrupted strain was named H16 ΔphaC1 Ptrc-phaJ4b dZ1,2,6 strain.

The obtained H16 ΔphaC1 Ptrc-phaJ4b dZ1,2,6 strain is a strain in which a region from the start codon to the stop codon of the phaZ1 gene and the phaZ6 gene on a chromosome of *Cupriavidus necator* H16 strain is deleted, a region from 16th codon to the stop codon of the phaZ2 gene is deleted, expression of a R-body-specific enoyl-CoA hydratase gene on the chromosome is intensified, and a region from the start codon to the stop codon of the phaC1 gene is deleted.

(Production Example 2) Preparation of pCUP2-Ptrp-NSDG

A DNA fragment having the nucleotide sequence of SEQ ID NO: 13 was amplified by PCR using a synthetic oligo DNA or the like. Using In-fusion HD Cloning Kit (Takara Bio Inc.), the obtained DNA fragment was linked to a DNA fragment obtained by digesting the pCUP2 vector described in Japanese Patent Laid-Open No. 2007-259708 with MunI and SpeI. In this way pCUP2-Ptrp-NSDG was obtained.

The obtained pCUP2-Ptrp-NSDG is a plasmid that expresses NSDG under the trp promoter.

NSDG is a mutant PHA synthase which consists of the amino acid sequence of SEQ ID NO: 14 and which is obtained by introducing two mutations of substitution of asparagine at the 149th position from the N-terminus with serine and substitution of asparagine at the 171st position from the N-terminus with glycine into the amino acid sequence of the SEQ ID NO: 1.

(Production Example 3) Preparation of pCUP2-Ptrp-NSDG-S389X

PCR was carried out using the pCUP2-Ptrp-NSDG, which had been prepared in Production Example 2, as a template and using the DNAs of SEQ ID NOS: 15 and 16 as a primer pair. Similarly, PCR was performed using the DNAs of SEQ ID NOS: 17 and 18 as a primer pair. A DNA fragment was obtained by carrying out PCR under similar conditions using the two DNA fragments, which had been obtained by the PCR, as templates and using the DNAs of SEQ ID NOS: 15 and 18 as a primer pair. This DNA fragment was linked to a DNA fragment obtained by digesting the pCUP2 vector with MunI and SpeI using an In-fusion HD Cloning Kit, and introduced into *Escherichia coli* JM109 Competent Cell (Takara Bio Inc.). Plasmids were recovered from each *Escherichia coli* colony and DNA sequences were identified to obtain pCUP2-Ptrp-NSDG-S389X. Here, X represents amino acids A, C, D, E, F, Q H, I, K, L, M, N, P, Q, R, T, V, W, or Y The obtained pCUP2-Ptrp-NSDG-S389X is a plasmid that expresses, under the trp promoter, NSDG having a mutation of substitution of serine at the 389th position from the N-terminus with X.

(Production Example 4) Preparation of pCUP2-Ptrp-NSDG-L436X

PCR was carried out using the pCUP2-Ptrp-NSDG, which had been prepared in Production Example 2, as a template and using the DNAs of SEQ ID NOS: 15 and 19 as a primer pair. Similarly, PCR was performed using the DNAs of SEQ ID NOS: 20 and 18 as a primer pair. A DNA fragment was obtained by carrying out PCR under similar conditions using the two DNA fragments, which had been obtained by the PCR, as templates and using the DNAs of SEQ ID NOS: 15 and 18 as a primer pair. This DNA fragment was linked to a DNA fragment obtained by digesting the pCUP2 vector with MunI and SpeI using an In-fusion HD Cloning Kit, and introduced into *Escherichia coli* JM109 Competent Cell (Takara Bio Inc.). Plasmids were recovered from each *Escherichia coli* colony and DNA sequences were identified to obtain pCUP2-Ptrp-NSDG-L436X. Here, X represents amino acids A, C, D, E, F, Q H, I, K, M, N, P, Q, R, T, V, W, or Y The obtained pCUP2-Ptrp-NSDG-L436X is a plasmid that expresses, under the trp promoter, NSDG having a mutation of substitution of leucine at the 436th position from the N-terminus with X.

(Production Example 5) Preparation of pCUP2-Ptrp-NSDGΔCT5

PCR was carried out using the pCUP2-Ptrp-NSDG which had been prepared in Production Example 2, as a template and using the DNAs of SEQ ID NOS: 15 and 21 as a primer pair. Using In-fusion HD Cloning Kit, the obtained DNA fragment was linked to a DNA fragment obtained by digesting the pCUP2 vector with MunI and SpeI. In this way pCUP2-Ptrp-NSDGΔCT5 was obtained. The obtained pCUP2-Ptrp-NSDGΔCT5 is a plasmid that expresses, under the trp promoter, NSDG having a mutation of deletion of five amino acid residues from the C-terminus.

(Production Example 6) Preparation of pCUP2-Ptrp-NSDGΔCT10

PCR was carried out using the pCUP2-Ptrp-NSDG, which had been prepared in Production Example 2, as a template and using the DNAs of SEQ ID NOS: 15 and 22 as a primer pair. Using In-fusion HD Cloning Kit, the obtained DNA fragment was linked to a DNA fragment obtained by digesting the pCUP2 vector with MunI and SpeI. In this way pCUP2-Ptrp-NSDGΔCT10 was obtained. The obtained pCUP2-Ptrp-NSDGΔCT10 is a plasmid that expresses, under the trp promoter, NSDG having a mutation of deletion of 10 amino acid residues from the C-terminus.

(Production Example 7) Preparation of pCUP2-Ptrp-NSDGΔCT13

PCR was carried out using the pCUP2-Ptrp-NSDG, which had been prepared in Production Example 2, as a template and using the DNAs of SEQ ID NOS: 15 and 23 as a primer pair. Using In-fusion HD Cloning Kit, the obtained DNA fragment was linked to a DNA fragment obtained by digesting the pCUP2 vector with MunI and SpeI. In this way pCUP2-Ptrp-NSDGΔCT13 was obtained. The obtained pCUP2-Ptrp-NSDGΔCT13 is a plasmid that expresses, under the trp promoter, NSDG having a mutation of deletion of 13 amino acid residues from the C-terminus.

(Production Example 8) Preparation of pCUP2-Ptrp-NSDGΔCT15

PCR was carried out using the pCUP2-Ptrp-NSDG, which had been prepared in Production Example 2, as a template and using the DNAs of SEQ ID NOS: 15 and 24 as a primer pair. Using In-fusion HD Cloning Kit, the obtained DNA fragment was linked to a DNA fragment obtained by digesting the pCUP2 vector with MunI and SpeI. In this way pCUP2-Ptrp-NSDGΔCT15 was obtained. The obtained pCUP2-Ptrp-NSDGΔCT15 is a plasmid that expresses, under the trp promoter, NSDG having a mutation of deletion of 15 amino acid residues from the C-terminus.

(Production Example 9) Preparation of pCUP2-Ptrp-NSDGΔCT20

PCR was carried out using the pCUP2-Ptrp-NSDG, which had been prepared in Production Example 2, as a template and using the DNAs of SEQ ID NOS: 15 and 25 as a primer pair. Using In-fusion HD Cloning Kit, the obtained DNA fragment was linked to a DNA fragment obtained by digesting the pCUP2 vector with MunI and SpeI. In this way pCUP2-Ptrp-NSDGΔCT20 was obtained. The obtained pCUP2-Ptrp-NSDGΔCT20 is a plasmid that expresses, under the trp promoter, NSDG having a mutation of deletion of 20 amino acid residues from the C-terminus.

(Production Example 10) Preparation of H16 ΔphaC1 Ptrc-phaJ4b dZ1,2,6/pCUP2-Ptrp-NSDG Strain First, the H16 ΔphaC1 Ptrc-phaJ4b dZ1,2,6 strain prepared in Production Example 1 was cultured overnight in Nutrient Broth medium (DIFCO). 0.5 mL of the obtained culture solution was inoculated in 100 mL of Nutrient Broth medium, and cultured at 30° C. for 3 hours. The obtained culture solution was quickly cooled on ice, the bacterial cells were collected, and washed thoroughly with ice-cooled distilled water, and the obtained bacterial cells were suspended in 2 mL of distilled water. The bacterial cell liquid was mixed with the pCUP2-Ptrp-NSDG plasmid solution prepared in Production Example 2, and the mixture was poured into a cuvette to perform electroporation. Electroporation was performed under the conditions of a voltage of 1.5 kV, a resistance of 8009 and a current of 25 μF using a MicroPulser electroporator (Bio Rad Inc.). After the electroporation, the bacterial cell solution was recovered, 5 mL of Nutrient Broth medium was added, and the mixture was cultured at 30° C. for 3 hours. The obtained culture solution was applied to Nutrient Agar medium containing 100 mg/L kanamycin sulfate. The culture was performed at 30° C. for 3 days, and a strain containing a plasmid was obtained from the resulting colonies. The obtained strain was named H16 ΔphaC1 Ptrc-phaJ4b dZ1,2,6/pCUP2-Ptrp-NSDG strain.

(Production Example 11) Preparation of H16 ΔphaC1 Ptrc-phaJ4b dZ1,2,6/pCUP2-Ptrp-NSDG-S389X Strain In the same manner as in Production Example 10, the pCUP2-Ptrp-NSDG-S389X prepared in Production Example 3 was introduced using the H16 ΔphaC1 Ptrc-phaJ4b dZ1,2,6 strain, which had been prepared in Production Example 1, as a parent strain. The obtained strain was named H16 ΔphaC1 Ptrc-phaJ4b dZ1,2,6/pCUP2-Ptrp-NSDG-S389X strain.

(Production Example 12) Preparation of H16 ΔphaC1 Ptrc-phaJ4b dZ1,2,6/pCUP2-Ptrp-NSDG-L436X Strain In the same manner as in Production Example 10, the pCUP2-Ptrp-NSDG-L436X prepared in Production Example 4 was introduced using the H16 ΔphaC1 Ptrc-phaJ4b dZ1,2,6 strain, which had been prepared in Production Example 1, as a parent strain. The obtained strain was named H16 ΔphaC1 Ptrc-phaJ4b dZ1,2,6/pCUP2-Ptrp-NSDG-L436X strain.

(Production Example 13) Preparation of H16 ΔphaC1 Ptrc-phaJ4b dZ1,2,6/pCUP2-Ptrp-NSDGΔCT5 Strain In the same manner as in Production Example 10, the pCUP2-Ptrp-NSDGΔCT5 prepared in Production Example 5 was introduced using the H16 ΔphaC1 Ptrc-phaJ4b dZ1,2,6 strain, which had been prepared in Production Example 1, as a parent strain. The obtained strain was named H16 ΔphaC1 Ptrc-phaJ4b dZ1,2,6/pCUP2-Ptrp-NSDGΔCT5 strain.

(Production Example 14) Preparation of H16 ΔphaC1 Ptrc-phaJ4b dZ1,2,6/pCUP2-Ptrp-NSDGΔCT10 Strain In the same manner as in Production Example 10, the pCUP2-Ptrp-NSDGΔCT10 prepared in Production Example 6 was introduced using the H16 ΔphaC1 Ptrc-phaJ4b dZ1,2,6 strain, which had been prepared in Production Example 1, as a parent strain. The obtained strain was named H16 ΔphaC1 Ptrc-phaJ4b dZ1,2,6/pCUP2-Ptrp-NSDGΔCT10 strain.

(Production Example 15) Preparation of H16 ΔphaC1 Ptrc-phaJ4b dZ1,2,6/pCUP2-Ptrp-NSDGΔCT13 Strain In the same manner as in Production Example 10, the pCUP2-Ptrp-NSDGΔCT13 prepared in Production Example 7 was introduced using the H16 ΔphaC1 Ptrc-phaJ4b dZ1,2,6 strain, which had been prepared in Production Example 1, as a parent strain. The obtained strain was named H16 ΔphaC1 Ptrc-phaJ4b dZ1,2,6/pCUP2-Ptrp-NSDGΔCT13 strain.

(Production Example 16) Preparation of H16 ΔphaC1 Ptrc-phaJ4b dZ1,2,6/pCUP2-Ptrp-NSDGΔCT15 Strain In the same manner as in Production Example 10, the pCUP2-Ptrp-NSDGΔCT15 prepared in Production Example 8 was introduced using the H16 ΔphaC1 Ptrc-phaJ4b dZ1,2,6 strain, which had been prepared in Production Example 1, as a parent strain. The obtained strain was named H16 ΔphaC1 Ptrc-phaJ4b dZ1,2,6/pCUP2-Ptrp-NSDGΔCT15 strain.

(Production Example 17) Preparation of H16 ΔphaC1 Ptrc-phaJ4b dZ1,2,6/pCUP2-Ptrp-NSDGΔCT20 Strain In the same manner as in Production Example 10, the pCUP2-Ptrp-NSDGΔCT20 prepared in Production Example 9 was introduced using the H16 ΔphaC1 Ptrc-phaJ4b dZ1,2,6 strain, which had been prepared in Production Example 1, as a parent strain. The obtained strain was named H16 ΔphaC1 Ptrc-phaJ4b dZ1,2,6/pCUP2-Ptrp-NSDGΔCT20 strain.

(Method for Analysis of 3HH Ratio in PHA)

To about 20 mg of dried bacterial cells containing PHA, 1 mL of a sulfuric acid-methanol mixed liquid (15:85) and 1 mL of chloroform were added, the bottle was tightly capped, and the mixture was heated to 100° C. for 140 minutes to obtain methyl ester as a PHA degradation product. The product was cooled, 0.5 mL of deionized water was then added thereto, and the mixture was thoroughly stirred, and then left standing until the aqueous layer and the organic layer were separated. Thereafter, the monomer unit composition of the PHA degradation product in the separated organic layer was analyzed by capillary gas chromatography. The 3HH ratio was calculated from the obtained peak area.

GC-17A manufactured by Shimadzu Corporation was used as a gas chromatography, and NEUTRA BOND-1 (column length: 25 m, column inner diameter: 0.25 mm and liquid film thickness: 0.4 μm) manufactured by GL Science Inc. He was used as a carrier gas, the column inlet pressure was set to 100 kPa, and 1 μL of the sample was injected. The temperature was raised from the initial temperature of 50° C. to 200° C. at a rate of 8° C./min, and raised from 200° C. to 290° C. at a rate of 30° C./min.

(Comparative Example 1) Production of PHA by H16 ΔphaC1 Ptrc-phaJ4b dZ1,2,6/pCUP2-Ptrp-NSDG Strain The seed medium had a composition of meat extract: 10 g/L, bactotryptone: 10 g/L, yeast extract: 2 g/L, sodium dihydrogen phosphate dodecahydrate: 9 g/L and dipotassium hydrogen phosphate: 1.5 g/L.

The PHA production medium had a composition of disodium hydrogen phosphate dodecahydrate: 11 g/L, dipotassium hydrogen phosphate: 1.9 g/L, ammonium sulfate: 1.3 g/L, magnesium solution: 5 mL/L and a minute-amount metal salt solution: 1 mL/L. The magnesium solution was prepared by dissolving 200 g/L magnesium sulfate heptahydrate in water. The minute-amount metal salt solution was prepared by dissolving 0.218 g/L cobalt chloride hexahydrate, 16.2 g/L iron (III) chloride hexahydrate, 10.3 g/L calcium chloride dihydrate, 0.118 g/L nickel chloride hexahydrate and 0.156 g/L copper sulfate pentahydrate in 0.1 N hydrochloride.

50 μL of a glycerol stock solution of the H16 ΔphaC1 Ptrc-phaJ4b dZ1,2,6/pCUP2-Ptrp-NSDG strain prepared in Production Example 10 was inoculated in 10 mL of a seed medium, and cultured with shaking at 30° C. for 24 hours. The obtained culture solution was used as a pre-culture solution.

PHA production culture was performed in flasks. 50 mL of the PHA production medium was put in a 500 mL shaking flask. Immediately before inoculation, 250 μL of the magnesium solution, 50 μL of the minute-amount metal solution, and 1 g of palm kernel oil were added. After the medium was prepared, 500 μL of the pre-culture solution was inoculated in the shaking flask, and cultured with shaking at 30° C. for 72 hours. After completion of the culture, the bacterial cells were recovered from 10 mL of the culture solution, washed with ethanol, and vacuum-dried at 60° C. to obtain dried bacterial cells containing PHA, and the weight of the dried bacterial cells was measured. Table 1 shows the results of the dried bacterial cell weight and the 3HH ratio.

(Examples 1 to 13 and Comparative Examples 2 to 7) Production of PHA by H16 ΔphaC1 Ptrc-phaJ4b dZ1,2,6/pCUP2-Ptrp-NSDG-S389X Strain Using the H16 ΔphaC1 Ptrc-phaJ4b dZ1,2,6/pCUP2-Ptrp-NSDG-S389X strain prepared in Production Example 11, culture was performed in the same manner as in Comparative Example 1, and the weight of dried bacterial cells and the 3HH ratio were analyzed. Table 1 shows the results.

and tryptophan (W) (Examples 1 to 9), respectively, there was a decrease in 3HH ratio as compared to Comparison Example 1. On the other hand, in the four mutants obtained by substitution of serine at the 389th position with cysteine (C), isoleucine (I), threonine (T) and valine (V) (Examples 10 to 13), respectively, there was an increase in 3HH ratio. However, in the six mutants obtained by substitution of serine at the 389th position with alanine (A), phenylalanine (F), leucine (L), methionine (M), glutamine (Q) and tyrosine (Y) (Comparative Examples 2 to 7), respectively, there was no significant change in 3HH ratio.

The above results show that a PHA synthase having a mutation of substitution of serine at the 389th position in the amino acid sequence of SEQ ID NO: 1 with aspartic acid, glutamic acid, glycine, histidine, lysine, asparagine, proline, arginine or tryptophan is useful for producing PHA with a low 3HH ratio while maintaining polymer productivity, and a PHA synthase having a mutation of substitution of serine at the 389th position in the above-mentioned amino acid sequence with cysteine, isoleucine, threonine or valine is useful for producing PHA with a high 3HH ratio while maintaining polymer productivity.

TABLE 1

| | Host | Plasmid | Weight of dried bacterial cells (g/L) | 3HH Ratio (mol %) |
|---|---|---|---|---|
| Example 1 | H16 | pCUP2-Ptrp-NSDG-S389D | 16.3 | 11.3 |
| Example 2 | ΔphaC1 | pCUP2-Ptrp-NSDG-S389E | 18.9 | 10.3 |
| Example 3 | P$_{trc}$-phaJ4b | pCUP2-Ptrp-NSDG-S389G | 18.0 | 12.1 |
| Example 4 | ΔphaZ1,2,6 | pCUP2-Ptrp-NSDG-S389H | 20.9 | 12.4 |
| Example 5 | | pCUP2-Ptrp-NSDG-S389K | 16.6 | 4.0 |
| Example 6 | | pCUP2-Ptrp-NSDG-S389N | 21.1 | 14.0 |
| Example 7 | | pCUP2-Ptrp-NSDG-S389P | 17.8 | 6.1 |
| Example 8 | | pCUP2-Ptrp-NSDG-S389R | 19.2 | 5.8 |
| Example 9 | | pCUP2-Ptrp-NSDG-S389W | 20.4 | 12.7 |
| Example 10 | | pCUP2-Ptrp-NSDG-S389C | 20.6 | 17.2 |
| Example 11 | | pCUP2-Ptrp-NSDG-S389I | 22.4 | 16.1 |
| Example 12 | | pCUP2-Ptrp-NSDG-S389T | 18.1 | 15.6 |
| Example 13 | | pCUP2-Ptrp-NSDG-S389V | 20.0 | 18.0 |
| Comparative Example 1 | | pCUP2-Ptrp-NSDG | 20.6 | 14.9 |
| Comparative Example 2 | | pCUP2-Ptrp-NSDG-S389A | 22.1 | 14.9 |
| Comparative Example 3 | | pCUP2-Ptrp-NSDG-S389F | 20.1 | 15.2 |
| Comparative Example 4 | | pCUP2-Ptrp-NSDG-S389L | 22.9 | 15.2 |
| Comparative Example 5 | | pCUP2-Ptrp-NSDG-S389M | 22.2 | 14.9 |
| Comparative Example 6 | | pCUP2-Ptrp-NSDG-S389Q | 20.7 | 14.8 |
| Comparative Example 7 | | pCUP2-Ptrp-NSDG-S389Y | 19.7 | 14.7 |

<Discussion>

The results in Table 1 show that substitution of serine at the 389th position in the amino acid sequence of SEQ ID NO: 14 with any amino acid does not cause a significant change in the weight of dried bacterial cells. This indicates that there is no dramatic change in polymer production amount.

Comparison of the 3HH ratios of PTA shows that in the nine mutants obtained by substitution of serine at the 389th position in the amino acid sequence of SEQ ID NO: 14 with aspartic acid (D), glutamic acid (E), glycine (G), histidine (HI), lysine (K), asparagine (N), proline (P), arginine (R)

(Examples 14 to 21 and Comparative Examples 8 to 18) Production of PIA by H16 ΔphaC1 Ptrc-phap4b dZ1,2,6/pCUP2-Ptrp-NSDG-L436X Strain Using the H16 ΔphaC1 Ptrc-pha24b dZ-1,2,6/pCUP2-Ptrp-NSDG-L436X strain prepared in Production Example 12, culture was performed in the same manner as in Comparative Example 1, and the weight of dried bacterial cells and the 3HH ratio were analyzed. Table 2 shows the results.

TABLE 2

| | Host | Plasmid | Weight of dried bacterial cells (g/L) | 3HH Ratio (mol %) |
|---|---|---|---|---|
| Example 14 | H16 | pCUP2-Ptrp-NSDG-L436A | 13.7 | 11.0 |
| Example 15 | ΔphaC1 | pCUP2-Ptrp-NSDG-L436C | 20.9 | 13.8 |
| Example 16 | $P_{trc}$-phaJ4b | pCUP2-Ptrp-NSDG-L436F | 22.8 | 9.8 |
| Example 17 | ΔphaZ1,2,6 | pCUP2-Ptrp-NSDG-L436N | 13.5 | 8.2 |
| Example 18 | | pCUP2-Ptrp-NSDG-L436T | 21.6 | 14.3 |
| Example 19 | | pCUP2-Ptrp-NSDG-L436W | 17.9 | 6.9 |
| Example 20 | | pCUP2-Ptrp-NSDG-L436Y | 15.8 | 4.8 |
| Example 21 | | pCUP2-Ptrp-NSDG-L436V | 22.1 | 15.6 |
| Comparative Example 1 | | pCUP2-Ptrp-NSDG | 20.6 | 14.9 |
| Comparative Example 8 | | pCUP2-Ptrp-NSDG-L436D | 4.1 | — |
| Comparative Example 9 | | pCUP2-Ptrp-NSDG-L436E | 5.2 | 3.4 |
| Comparative Example 10 | | pCUP2-Ptrp-NSDG-L436G | 9.6 | 4.8 |
| Comparative Example 11 | | pCUP2-Ptrp-NSDG-L436H | 10.9 | 4.6 |
| Comparative Example 12 | | pCUP2-Ptrp-NSDG-L436I | 21.7 | 15.1 |
| Comparative Example 13 | | pCUP2-Ptrp-NSDG-L436K | 10.3 | 3.2 |
| Comparative Example 14 | | pCUP2-Ptip-NSDG-L436M | 22.6 | 14.7 |
| Comparative Example 15 | | pCUP2-Ptrp-NSDG-L436P | 3.7 | — |
| Comparative Example 16 | | pCUP2-Pttp-NSDG-L436Q | 10.6 | 7.2 |
| Comparative Example 17 | | pCUP2-Ptrp-NSDG-L436R | 3.6 | — |
| Comparative Example 18 | | pCUP2-Ptrp-NSDG-L436S | 10.7 | 7.7 |

<Discussion>

The results in Table 2 show that in the nine mutants obtained by substitution of leucine at the 436th position in the amino acid sequence of SEQ ID NO: 14 with aspartic acid (D), glutamic acid (E), glycine (G), histidine (H), lysine (K), proline (P), glutamine (Q), arginine (R) and serine (S) (Comparative Examples 8 to 11, 13 and 15 to 18), respectively, there was a significant decrease in the weight of dried bacterial cells as compared to Comparative Example 1, and this indicates that polymer productivity was reduced. In the mutants obtained by substitution of leucine (I) at the 436th position with isoleucine (I) and methionine (M) (Comparative Examples 12 and 14), respectively, there was no change in any of the weight of dried bacterial cells and the 3HH ratio as compared to Comparative Example 1.

On the other hand, in the mutants obtained by substitution of leucine at the 436th position with alanine (A), cysteine (C), phenylalanine (F), asparagine (N), threonine (T), tryptophan (W) and tyrosine (Y) (Examples 14 to 20), respectively, there was no significant change in the weight of dried bacterial cells and a decrease in 3HH ratio as compared to Comparative Example 1. In the mutant obtained by substitution of leucine at the 436th position with valine (V) (Example 21), there was no significant change in the weight of dried bacterial cells and an increase in 3HH ratio as compared to Comparative Example 1.

The above results show that a PHA synthase having a mutation of substitution of leucine at the 436th position in the amino acid sequence of SEQ ID NO: 1 with alanine, cysteine, phenylalanine, asparagine, threonine, tryptophan or tyrosine is useful for producing PHA with a low 3HH ratio while maintaining polymer productivity, and a PHA synthase having a mutation of substitution of leucine at the 436th position in the above-mentioned amino acid sequence with valine is useful for producing PHA with a high 3HH ratio while maintaining polymer productivity.

(Examples 23 and 24 and Comparative Examples 19 to 21) Production of PHA by H16 ΔphaC1 Ptrc-phaJ4b dZ1,2,6/pCUP2-Ptrp-NSDGΔC5, ΔC10, ΔC13, ΔC15 or ΔC20 Strain Using the H16 ΔphaC1 Ptrc-phaJ4b dZ1,2,6/pCUP2-Ptrp-NSDGΔC5, ΔC10, ΔC13, ΔC15 or ΔC20 strain prepared in Production Examples 13 to 17, culture was performed in the same manner as in Comparative Example 1, and the weight of dried bacterial cells and the 3HH ratio were analyzed. Table 3 shows the results.

TABLE 3

| | Host | Plasmid | Weight of dried bacterial cells (g/L) | 3HH Ratio (mol %) |
|---|---|---|---|---|
| Example 22 | H16 | pCUP2-Ptrp-NSDG-ΔCT13 | 24.2 | 13.1 |
| Example 23 | ΔphaC1 | pCUP2-Ptrp-NSDG-ΔCT15 | 21.3 | 10.2 |
| Comparative Example 1 | $P_{trc}$-phaJ4b ΔphaZ1,2,6 | pCUP2-Ptrp-NSDG | 20.6 | 14.9 |

TABLE 3-continued

| Host | Plasmid | Weight of dried bacterial cells (g/L) | 3HH Ratio (mol %) |
|---|---|---|---|
| Comparative Example 19 | pCUP2-Ptip-NSDGΔCT5 | 24.0 | 15.3 |
| Comparative Example 20 | pCUP2-Ptrp-NSDGΔCT10 | 20.7 | 15.5 |
| Comparative Example 21 | pCUP2-Ptrp-NSDGΔCT20 | 4.2 | — |

<Discussion>

The results in Table 3 show that in the mutant obtained by deletion of five amino acid residues from the C-terminus of the amino acid sequence of SEQ ID NO: 14 (Comparative Example 19) and the mutant obtained by deletion of 10 amino acid residues from the C-terminus (Comparative Example 20), there was no change in any of the weight of dried bacterial cells and the 3HH ratio as compared to Comparative Example 1, and in the mutant obtained by deletion of 20 amino acid residues from the C-terminus (Comparative Example 21), there was a significant decrease in the weight of dried bacterial cells. However, in the mutant obtained by deletion of 13 amino acid residues from the C-terminus (Example 22) and the mutant obtained by deletion of 15 amino acid residues from the C-terminus (Example 23), there was no significant change in the weight of dried bacterial cells, and there was a decrease in 3HH ratio.

The above results show that a PHA synthase having a mutation of deletion of an appropriate number of amino acid residues from the C-terminus of the amino acid sequence of SEQ ID NO: 1 is useful for producing PHA with a low 3HH ratio while maintaining polymer productivity.

The invention claimed is:

1. A mutant polyhydroxyalkanoate synthase comprising an amino acid sequence having at least 90% sequence identity with the amino acid sequence of SEQ ID NO: 1, wherein the amino acid sequence of the mutant polyhydroxyalkanoate synthase comprises a substitution of asparagine at 149th position from the N-terminus of the amino acid sequence of SEQ ID NO: 1 with serine and a substitution of aspartic acid at 171st position from the N-terminus of the amino acid sequence of SEQ ID NO: 1 with glycine, and
further comprises at least one mutation selected from the group consisting of (a), (b), and (c):
(a) a substitution of serine at 389th position from N-terminus of the amino acid sequence of SEQ ID NO: 1 with an amino acid other than serine;
(b) a substitution of leucine at 436th position from the N-terminus of the amino acid sequence of SEQ ID NO: 1 with an amino acid other than leucine; and
(c) a deletion of from 11 to 19 amino acid residues from the C-terminus of the amino acid sequence of SEQ ID NO: 1.

2. The mutant polyhydroxyalkanoate synthase according to claim 1, wherein in the mutation (a) serine at the 389th position from the N-terminus of the amino acid sequence of SEQ ID NO: 1 is substituted with cysteine, isoleucine, threonine or valine.

3. The mutant polyhydroxyalkanoate synthase according to claim 1, wherein in the mutation (a) serine at the 389th position from the N-terminus of the amino acid sequence of SEQ ID NO: 1 is substituted with aspartic acid, glutamic acid, glycine, histidine, lysine, asparagine, proline, arginine or tryptophan.

4. The mutant polyhydroxyalkanoate synthase according to claim 1, wherein in the mutation (b) leucine at the 436th position from the N-terminus of the amino acid sequence of SEQ ID NO: 1 is substituted with valine.

5. The mutant polyhydroxyalkanoate synthase according to claim 1, wherein in the mutation (b) leucine at the 436th position from the N-terminus of the amino acid sequence of SEQ ID NO: 1 is substituted with alanine, cysteine, phenylalanine, asparagine, threonine, tryptophan or tyrosine.

6. The mutant polyhydroxyalkanoate synthase according to claim 1, wherein in the mutation (c) 12 to 19 amino acid residues from the C-terminus of the amino acid sequence of SEQ ID NO: 1 are deleted.

7. A gene encoding the mutant polyhydroxyalkanoate synthase of claim 1.

8. A transformant comprising the gene of claim 7.

9. The transformant according to claim 8, wherein a host is a bacterium.

10. The transformant according to claim 9, wherein the bacterium is a bacterium belonging to *Cupriavidus*.

11. The transformant according to claim 9, wherein the bacterium is *Cupriavidus necator*.

12. The transformant according to claim 9, wherein the bacterium is *Cupriavidus necator* H16.

13. A method for producing polyhydroxyalkanoate, comprising culturing the transformant of claim 8.

14. The method for producing polyhydroxyalkanoate according to claim 13, wherein the polyhydroxyalkanoate comprises 3-hydroxyhexanoate as a monomer unit.

15. The method for producing polyhydroxyalkanoate according to claim 13, wherein the polyhydroxyalkanoate is a copolymer of 3-hydroxybutyrate and 3-hydroxyhexanoate.

16. The mutant polyhydroxyalkanoate synthase according to claim 1, wherein the mutant polyhydroxyalkanoate synthase comprises an amino acid sequence having at least 95% sequence identity with the amino acid sequence of SEQ ID NO: 1.

* * * * *

SEQUENCE LISTING

<160> NUMBER OF SEQ ID NOS: 25

<210> SEQ ID NO 1
<211> LENGTH: 594
<212> TYPE: PRT
<213> ORGANISM: Aeromonas caviae

<400> SEQUENCE: 1

```
Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205
```

Leu Ala Leu Thr Pro Gly Arg Val Val Gln Arg Thr Glu Leu Tyr Glu
210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
            245                 250                 255

Pro Gln Asn Ser Leu Val Ala Trp Leu Val Ala Gln Gly Gln Thr Val
        260                 265                 270

Phe Met Ile Ser Trp Arg Asn Pro Gly Val Ala Gln Gln Ile Asp
    275                 280                 285

Leu Asp Asp Tyr Val Val Asp Gly Val Ile Ala Leu Asp Gly Val
290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
            325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
            405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
            485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
        515                 520                 525

Glu Ser Trp Leu Ala Gly Ala Thr His Gln Gly Gly Ser Trp Trp Pro
530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
            565                 570                 575

Val Lys Val Arg Leu Asn Pro Val Phe Ala Cys Pro Thr Glu Glu Asp
            580                 585                 590

Ala Ala

<210> SEQ ID NO 2
<211> LENGTH: 842
<212> TYPE: DNA
<213> ORGANISM: Cupriavidus necator

<400> SEQUENCE: 2

```
cccgggcaag taccttgccg acatctatgc gctggcgcgc acgcgcctgg cgcgcgccgg      60
ctgtaccgag gtctacggcg gcgacgcctg caccgtggcc gacgccggtc gcttctactc     120
ctatcggcgc gatggcgtga ccggccgcat ggccagcctg gtctggctgg cggactgagc     180
ccgccgctgc ctcactcgtc cttgcccctg gccgcctgcg cgcgctcggc ttcagccttg     240
cgtcggcgg ggccgggcgt gcccatgatg tagagcacca cgccaccgg cgccatgcca      300
tacatcagga aggtggcaac gcctgccacc acgttgtgct cggtgatcgc catcatcagc     360
gccacgtaga gccagccaat ggccacgatg tacatcaaaa attcatcctt ctcgcctatg     420
ctctggggcc tcggcagatg cgagcgctgc ataccgtccg gtaggtcggg aagcgtgcag     480
tgccgaggcg gattcccgca ttgacagcgc gtgcgttgca aggcaacaat ggactcaaat     540
gtctcggaat cgctgacgat tcccaggttt ctccggcaag catagcgcat ggcgtctcca     600
tgcgagaatg tcgcgcttgc cggataaaag gggagccgct atcggaatgg acgcaagcca     660
cggccgcagc aggtgcggtc gagggcttcc agccagttcc agggcagatg tgccggcaga     720
ccctccccgct ttgggggagg cgcaagccgg gtccattcgg atagcatctc cccatgcaaa    780
gtgccggcca gggcaatgcc cggagccggt tcgaatagtg acggcagaga gacaatcaaa     840
tc                                                                    842
```

<210> SEQ ID NO 3
<211> LENGTH: 268
<212> TYPE: DNA
<213> ORGANISM: Cupriavidus necator

<400> SEQUENCE: 3

```
catggccctc gccggagcgc cccggagtgg cgtcacagcc gctcccgtgt atcgccagca      60
acgttgtttg tgcattgcac aaaatccact tgacattgga tctggcgccc ctaaaatagg     120
aattgttgcg gcgcaccaaa taagaaatgc gccttgaccc acccacacgc ctgggctggc     180
cgaatcgggc acaacaccgt cacggccctg acatctaggc ggcttaattt gctagacctt     240
gaagttcacc actggagacc agcaattg                                        268
```

<210> SEQ ID NO 4
<211> LENGTH: 123
<212> TYPE: DNA
<213> ORGANISM: Escherichia coli

<400> SEQUENCE: 4

```
gcgcaacgca attaatgtga gttagctcac tcattaggca ccccaggctt tacactttat      60
gcttccggct cgtatgttgt gtggaattgt gagcggataa caatttcaca caggaaacaa     120
ttg                                                                    123
```

<210> SEQ ID NO 5
<211> LENGTH: 232
<212> TYPE: DNA
<213> ORGANISM: Escherichia coli

<400> SEQUENCE: 5

```
tgcttctggc gtcaggcagc catcggaagc tgtggtatgg ctgtgcaggt cgtaaatcac      60
tgcataattc gtgtcgctca aggcgcactc ccgttctgga taatgttttt tgcgccgaca     120
tcataacggt tctggcaaat attctgaaat gagctgttga caattaatca tcgaactagt     180
```

```
taactagtac gcaagttcac agcggataac aatttcacac aggaaacaat tg          232
```

<210> SEQ ID NO 6
<211> LENGTH: 123
<212> TYPE: DNA
<213> ORGANISM: Artificial Sequence
<220> FEATURE:
<223> OTHER INFORMATION: Artificial promoter

<400> SEQUENCE: 6

```
gcgcaacgca attaatgtga gttagctcac tcattaggca ccccaggctt tacactttat   60
gcttccggct cgtataatgt gtggaattgt gagcggataa caatttcaca caggaaacaa  120
ttg                                                                123
```

<210> SEQ ID NO 7
<211> LENGTH: 236
<212> TYPE: DNA
<213> ORGANISM: Artificial Sequence
<220> FEATURE:
<223> OTHER INFORMATION: Artificial promoter

<400> SEQUENCE: 7

```
caattgtgct tctggcgtca ggcagccatc ggaagctgtg gtatggctgt gcaggtcgta   60
aatcactgca taattcgtgt cgctcaaggc gcactcccgt tctggataat gttttttgcg  120
ccgacatcat aacggttctg gcaaatattc tgaaatgagc tgttgacaat taatcatccg  180
gctcgtataa tgtgtggaat tgtgagcgga taacaatttc acaggaaa caattg        236
```

<210> SEQ ID NO 8
<211> LENGTH: 237
<212> TYPE: DNA
<213> ORGANISM: Artificial Sequence
<220> FEATURE:
<223> OTHER INFORMATION: Artificial promoter

<400> SEQUENCE: 8

```
caattgtgct tctggcgtca ggcagccatc ggaagctgtg gtatggctgt gcaggtcgta   60
aatcactgca taattcgtgt cgctcaaggc gcactcccgt tctggataat gttttttgcg  120
ccgacatcat aacggttctg gcaaatattc tgaaatgagc tgttgacaat taatcatcgc  180
ggctcgtata atgtgtggaa ttgtgagcgg ataacaattt cacacaggaa acaattg     237
```

<210> SEQ ID NO 9
<211> LENGTH: 235
<212> TYPE: DNA
<213> ORGANISM: Artificial Sequence
<220> FEATURE:
<223> OTHER INFORMATION: Artificial promoter

<400> SEQUENCE: 9

```
caattgtgct tctggcgtca ggcagccatc ggaagctgtg gtatggctgt gcaggtcgta   60
aatcactgca taattcgtgt cgctcaaggc gcactcccgt tctggataat gttttttgcg  120
ccgacatcat aacggttctg gcaaatattc tgaaatgagc tgttgacaat taatcatcgg  180
ctcgtataat gtgtggaatt gtgagcggat aacaatttca caggaaac aattg         235
```

<210> SEQ ID NO 10
<211> LENGTH: 128
<212> TYPE: DNA
<213> ORGANISM: Artificial Sequence
<220> FEATURE:
<223> OTHER INFORMATION: Artificial promoter

<400> SEQUENCE: 10

```
caattggcgc aacgcaatta atgtgagtta gctcactcat taggcacccc aggctttaca      60
cttatgcttc cggctcgtat gttgtgtgga attgtgagcg ataacaatt tcacacagga     120
aacaattg                                                             128
```

<210> SEQ ID NO 11
<211> LENGTH: 24
<212> TYPE: DNA
<213> ORGANISM: Cupriavidus necator

<400> SEQUENCE: 11

```
cacgtgcaga gagacaatca aatc                                            24
```

<210> SEQ ID NO 12
<211> LENGTH: 1056
<212> TYPE: DNA
<213> ORGANISM: Artificial Sequence
<220> FEATURE:
<223> OTHER INFORMATION: Upstream and downstream sequence of phaC1 ORF
      derived from C. necator H16

<400> SEQUENCE: 12

```
gcgcgcattt aaatctgcca ccacgttgtg ctcggtgatc gccatcatca gcgccacgta      60
gagccagcca atggccacga tgtacatcaa aaattcatcc ttctcgccta tgctctgggg     120
cctcggcaga tgcgagcgct gcataccgtc cggtaggtcg ggaagcgtgc agtgccgagg     180
cggattcccg cattgacagc gcgtgcgttg caaggcaaca atggactcaa atgtctcgga     240
atcgctgacg attcccaggt ttctccggca agcatagcgc atggcgtctc catgcgagaa     300
tgtcgcgctt gccggataaa aggggagccg ctatcggaat ggacgcaagc cacggccgca     360
gcaggtgcgg tcgagggctt ccagccagtt ccagggcaga tgtgccggca gaccctcccg     420
ctttggggga ggcgcaagcc gggtccattc ggatagcatc tccccatgca aagtgccggc     480
cagggcaatg cccggagccg gttcgaatag tgacggcaga gagacaatca aatccgcttg     540
catgagtgcc ggcgtgcgtc atgcacggcg ccggcaggcc tgcaggttcc ctcccgtttc     600
cattgaaagg actacacaat gactgacgtt gtcatcgtat ccgccgcccg caccgcggtc     660
ggcaagtttg gcggctcgct ggccaagatc ccggcaccgg aactgggtgc cgtggtcatc     720
aaggccgcgc tggagcgcgc cggcgtcaag ccggagcagg tgagcgaagt catcatgggc     780
caggtgctga ccgccggttc gggccagaac cccgcacgcc aggccgcgat caaggccggc     840
ctgccggcga tggtgccggc catgaccatc aacaaggtgt gcggctcggg cctgaaggcc     900
gtgatgctgg ccgccaacgc gatcatggcg ggcgacgccg agatcgtggt ggccggcggc     960
caggaaaaca tgagcgccgc cccgcacgtg ctgccgggct cgcgcgatgg tttccgcatg    1020
ggcgatgcca agctggtcga caatttaaat gcgcgc                              1056
```

<210> SEQ ID NO 13
<211> LENGTH: 2122
<212> TYPE: DNA
<213> ORGANISM: Artificial Sequence
<220> FEATURE:
<223> OTHER INFORMATION: amplified sequence

<400> SEQUENCE: 13

```
cctagggtgt acattgcgct gaaagaaggg ccaattgtgc ttctggcgtc aggcagccat      60
cggaagctgt ggtatggctg tgcaggtcgt aaatcactgc ataattcgtg tcgctcaagg     120
```

-continued

```
cgcactcccg ttctggataa tgttttttgc gccgacatca taacggttct ggcaaatatt    180
ctgaaatgag ctgttgacaa ttaatcatcg aactagttaa ctagtacgca agttcacagc    240
ggataacaat ttcacacagg aaacaattgc acgtgcagag agacaatcaa atcatgagcc    300
aaccatctta tggcccgctg ttcgaggccc tggcccacta caatgacaag ctgctggcca    360
tggccaaggc ccagacagag cgcaccgccc aggcgctgct gcagaccaat ctggacgatc    420
tgggccaggt gctggagcag gcagccagc aaccctggca gctgatccag cccagatga    480 actggtggca ggatcagctc aagctgatgc agcacaccct gctcaaaagc gcaggccagc    540
cgagcgagcc ggtgatcacc ccggagcgca gcgatcgccg cttcaaggcc gaggcctgga    600
gcgaacaacc catctatgac tacctcaagc agtcctacct gctcaccgcc aggcacctgc    660
tggcctcggt ggatgccctg gagggcgtcc cccagaagag ccgggagcgg ctgcgtttct    720 tcaccccgcca gtacgtcagc gccatggccc ccagcaactt cctggccacc aaccccgagc    780
tgctcaagct gaccctggag tccggcggcc agaacctggt gcgcggactg gccctcttgg    840
ccgaggatct ggagcgcagc gccgatcagc tcaacatccg cctgaccgac gaatccgcct    900
tcgagctcgg gcgggatctg gccctgaccc cgggccgggt ggtgcagcgc accgagctct    960
atgagctcat tcagtacagc ccgactaccg agacggtggg caagacacct gtgctgatag    1020
tgccgccctt catcaacaag tactacatca tggacatgcg gccccagaac tccctggtcg    1080
cctggctggt cgcccagggc cagacggtat tcatgatctc ctggcgcaac ccgggcgtgg    1140
cccaggccca aatcgatctc gacgactacg tggtggatgg cgtcatcgcc gccctggacg    1200
gcgtggaggc ggccaccggc gagcgggagg tgcacggcat cggctactgc atcggcggca    1260
ccgccctgtc gctcgccatg ggctggctgg cggcgcggcg ccagaagcag cgggtgcgca    1320
ccgccaccct gttcactacc ctgctggact tctcccagcc cggggagctt ggcatcttca    1380
tccacgagcc catcatagcg cgcgctcgagg cgcaaaatga ggccaagggc atcatggacg    1440
ggcgccagct ggcggtctcc ttcagcctgc tgcgggagaa cagcctctac tggaactact    1500
acatcgacag ctacctcaag ggtcagagcc cggtggcctt cgatctgctg cactggaaca    1560
gcgacagcac caatgtggcg ggcaagaccc acaacagcct gctgcgccgt ctctacctgg    1620
agaaccagct ggtgaagggg gagctcaaga tccgcaacac ccgcatcgat ctcggcaagg    1680
tgaagacccc tgtgctgctg gtgtcggcgg tggacgatca catcgccctc tggcagggca    1740
cctggcaggg catgaagctg tttggcgggg agcagcgctt cctcctggcg gagtccggcc    1800
acatcgccgg catcatcaac ccgccggccg ccaacaagta cggcttctgg cacaacgggg    1860
ccgaggccga gagcccggag agctggctgg aggggcgac gcaccagggc ggctcctggt    1920
ggcccgagat gatgggcttt atccagaacc gtgacgaagg tcagagccc gtccccgcgc    1980 gggtcccgga ggaagggctg gcccccgccc ccggccacta tgtcaaggtg cggctcaacc    2040 ccgtgttttgc ctgcccaaca gaggaggacg ccgcatgagc ctgacctgcc ggcctggttc    2100
aaccagtcgg cagccgacta gt                                              2122
```

<210> SEQ ID NO 14
<211> LENGTH: 594
<212> TYPE: PRT
<213> ORGANISM: Artificial Sequence
<220> FEATURE:
<223> OTHER INFORMATION: Mutated protein derived from Aeromonas caviae

<400> SEQUENCE: 14

```
Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gln Asn Leu
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
```

```
                420             425             430
His Asn Ser Leu Leu Arg Arg Leu Tyr Leu Glu Asn Gln Leu Val Lys
            435                 440                 445

Gly Glu Leu Lys Ile Arg Asn Thr Arg Ile Asp Leu Gly Lys Val Lys
            450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Ser Trp Trp Pro
        530                 535                 540

Glu Met Met Gly Phe Ile Gln Asn Arg Asp Glu Gly Ser Glu Pro Val
545                 550                 555                 560

Pro Ala Arg Val Pro Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cctagggtgt acattgcgct                                               20

<210> SEQ ID NO 16
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(26)
<223> OTHER INFORMATION: n is a, c, g, or t

<400> SEQUENCE: 16
ctgttctccc gcagcaggct gaamnngacc gccagctggc gcccgt                  46

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
ttcagcctgc tgcgggagaa cag                                           23

<210> SEQ ID NO 18
<211> LENGTH: 31
<212> TYPE: DNA
<213> ORGANISM: Artificial Sequence
```

```
<220> FEATURE:
<223> OTHER INFORMATION: primer

<400> SEQUENCE: 18
gctcggatcc actagtcggc tgccgactgg t                                    31

<210> SEQ ID NO 19
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(25)
<223> OTHER INFORMATION: n is a, c, g, or t

<400> SEQUENCE: 19
tctccaggta gagacggcgc agmnngctgt tgtgggtctt gcccgc                    46

<210> SEQ ID NO 20
<211> LENGTH: 22
<212> TYPE: DNA
<213> ORGANISM: Artificial Sequence
<220> FEATURE:
<223> OTHER INFORMATION: primer

<400> SEQUENCE: 20
ctgcgccgtc tctacctgga ga                                              22

<210> SEQ ID NO 21
<211> LENGTH: 78
<212> TYPE: DNA
<213> ORGANISM: Artificial Sequence
<220> FEATURE:
<223> OTHER INFORMATION: primer

<400> SEQUENCE: 21
gctcggatcc actagtcggc tgccgactgg ttgaaccagg ccggcaggtc aggctcatgt     60
tgggcaggca aacacggg                                                   78

<210> SEQ ID NO 22
<211> LENGTH: 77
<212> TYPE: DNA
<213> ORGANISM: Artificial Sequence
<220> FEATURE:
<223> OTHER INFORMATION: primer

<400> SEQUENCE: 22
gctcggatcc actagtcggc tgccgactgg ttgaaccagg ccggcaggtc aggctcacac     60
ggggttgagc cgcacct                                                    77

<210> SEQ ID NO 23
<211> LENGTH: 78
<212> TYPE: DNA
<213> ORGANISM: Artificial Sequence
<220> FEATURE:
<223> OTHER INFORMATION: primer

<400> SEQUENCE: 23
gctcggatcc actagtcggc tgccgactgg ttgaaccagg ccggcaggtc aggctcagag     60
ccgcaccttg acatagtg                                                   78

<210> SEQ ID NO 24
```

```
<211> LENGTH: 79
<212> TYPE: DNA
<213> ORGANISM: Artificial Sequence
<220> FEATURE:
<223> OTHER INFORMATION: primer

<400> SEQUENCE: 24
gctcggatcc actagtcggc tgccgactgg ttgaaccagg ccggcaggtc aggctcacac    60
cttgacatag tggccgggg                                                 79

<210> SEQ ID NO 25
<211> LENGTH: 74
<212> TYPE: DNA
<213> ORGANISM: Artificial Sequence
<220> FEATURE:
<223> OTHER INFORMATION: primer

<400> SEQUENCE: 25
gctcggatcc actagtcggc tgccgactgg ttgaaccagg ccggcaggtc aggctcagcc    60
gggggcgggg gcca                                                      74
```